United States Patent [19]

Small et al.

[11] Patent Number: 5,129,899

[45] Date of Patent: Jul. 14, 1992

[54] BONE FIXATION APPARATUS

[75] Inventors: Laura C. Small, Memphis, Tenn.; David L. Brumfield, Nesbit, Miss.; James W. Simmons, San Antonio, Tex.

[73] Assignee: Smith & Nephew Richards Inc., Memphis, Tenn.

[21] Appl. No.: 675,740

[22] Filed: Mar. 27, 1991

[51] Int. Cl.⁵ .......................... A61F 5/04; A61F 2/08; A61B 17/56; A61B 17/58
[52] U.S. Cl. .......................... 606/61; 606/71; 606/73; 623/13
[58] Field of Search .......................... 623/13; 606/60, 61, 606/64, 71, 73

[56] References Cited

U.S. PATENT DOCUMENTS

| | | | |
|---|---|---|---|
| 2,406,832 | 9/1946 | Hardinge | 606/71 |
| 4,246,660 | 1/1981 | Wevers | 623/13 |
| 4,887,595 | 12/1989 | Heinig et al. | 606/73 X |
| 4,987,892 | 1/1991 | Krag et al. | 606/61 |
| 5,041,113 | 8/1991 | Biedermann et al. | 606/61 |
| 5,053,036 | 10/1991 | Perren et al. | 606/71 X |

Primary Examiner—David Isabella
Assistant Examiner—Elizabeth M. Burke
Attorney, Agent, or Firm—Pravel, Gambrell, Hewitt, Kimball & Krieger

[57] ABSTRACT

A surgical spinal fixation system includes a bone bolt having first end portions that are adapted to be surgically implanted into a patient's spine at first and second spaced apart positions and a central portion of the bone bolt defining a load transfer surface, the bone bolt having a second upper threaded sections for threadably receiving a nut at a shaped, countersunk interface. As an alternate embodiment, a bone screw provides an upper enlarged head with a lower coarsely threaded shank. A plate having upper and lower surfaces and outer opposed edges is provided with an elongated slot for accommodating a selected bone bolt or bone screw. The plate edges carry fine adjustments extending between the upper and lower surfaces of the plate and a load transfer washer interfaces the plate and the selected bone bolt or bone screw for distributing load (and reducing stress) from the bone bolt (or screw) to the plate.

31 Claims, 3 Drawing Sheets

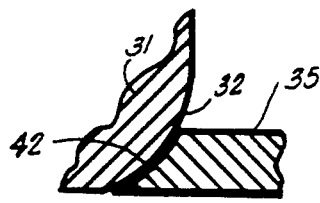
FIG. 1A
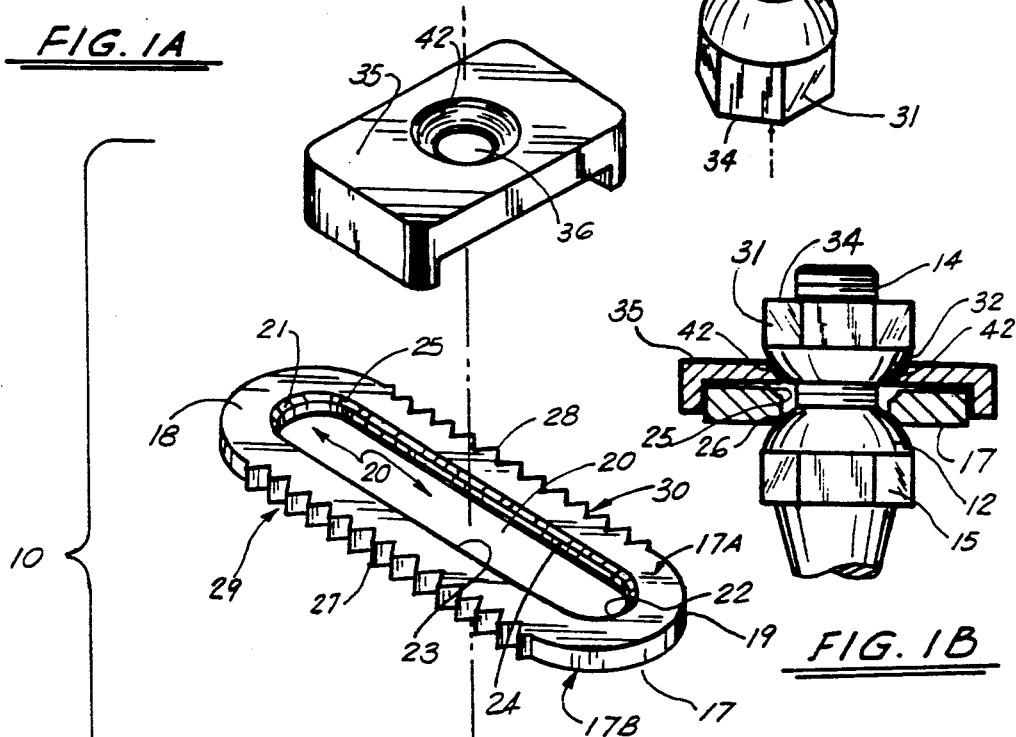
FIG. 1B
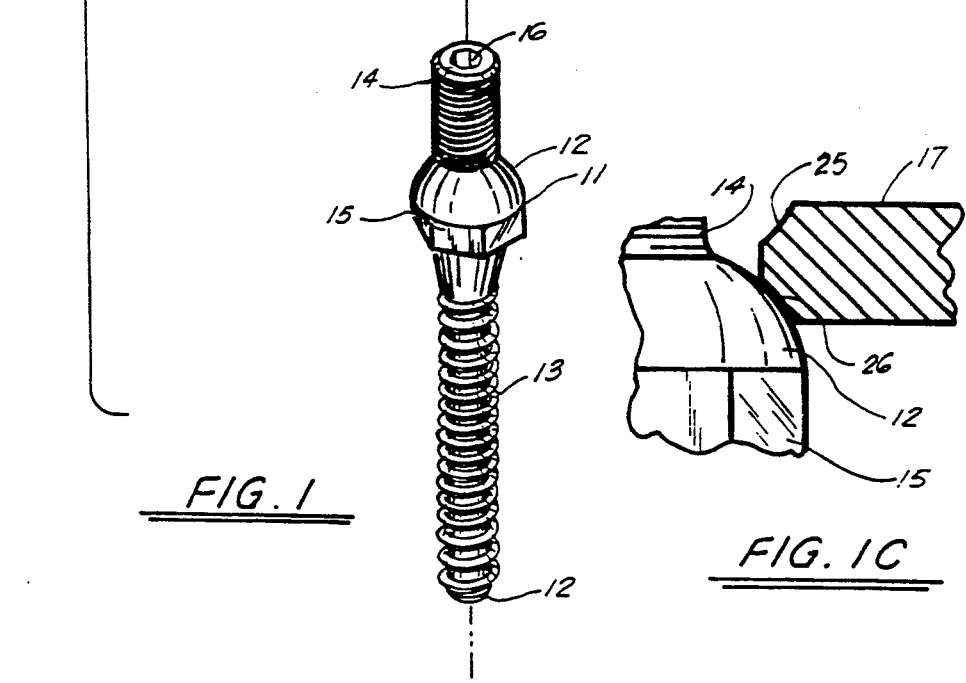
FIG. 1
FIG. 1C

BONE FIXATION APPARATUS

BACKGROUND OF THE INVENTION

1. Field Of The Invention

The present invention relates to surgical systems and more particularly relates to an improved bone or spinal fixation apparatus in the form of a strong and stable construct for maximum fusion augmentation with improved versatility and ease of use, and wherein an improved fine adjustment plate assembly forms a load transfer interface with an adjacent fixation bolt or screw. A countersunk interface provides some micromotion, better stress distribution and thus enhanced fatigue life.

2. General Background

There are a number of surgical procedures which require a fixation of portions of the spine with respect to one another. Typically, bone screws are employed in the fixation of the spine. The implantation of bone screws is a surgical procedure which involves the formation of one or more surgical openings in adjacent portions of the spine, with threaded bone screws being implanted into these surgical openings. Connective structure such as rods or plates extend between the various spine members by connecting the adjacent bone screws.

An early spinal fixation system can be seen in the Lumb et al. U.S. Pat. No. 3,648,691 entitled "Method of Applying Vertebral Appliance". In the Lumb patent, a method of applying a vertebral appliance for use in bridging one or more diseased or damaged vertebra uses a pair of elongated flexible multiple aperatured plates having fasteners which are used to clamp the plate to opposite sides of the spinous processes being spanned. Each strap or plate is of a length adapted to span at least two spinous processes and project there beyond each end so that the fasteners can be passed both behind and in front thereof as well as through the interspinous gap there between. The apertures are located considerably closer together than adjacent processes and they are fastened to the latter in position such that at least one opening registers with each one to receive a growth or soft bony tissue that eventually extrudes therein.

The Edwards U.S. Pat. No. 4,369,769 shows a spinal fixation system using elongated rods used to bridge across various portions of the spine. In the Edwards '769 patent a spinal fixation device is provided in which sleeves or spacers are placed over and around spinal rods in order to obtain a better reduction of spinal fractures or spinal deformities. These sleeves can be made in various thicknesses so that the surgeon can obtain optimum fixation in each case. The sleeves are made of any biologically compatible material.

Use of bone screws and connecting rods is also seen in the Ulrich et al. U.S. Pat. No. 4,433,677 entitled "Implantable Splint for Correction Lumbosacral Spondylodesis". In the Ulrich patent a spinal distraction splint has two like anchor screws extending along respective longitudinal screw axes and adapted to be anchored in the pelvis with the axes crossing. Each of the screws has a head formed with a transverse open recess centered on respective transverse axis and with an angular array of teeth centered on and angularly spaced about the respective transverse axis.

Another patent that shows screws as part of a spinal stabilizer is the Stephens et al. U.S. Pat. No. 4,604,995. In the Stephens patent a surgical implant is used for imparting stability to the thoraco-lumbar spine by fixation of the implant to the spine with segmental spinal instrumentation. The implant comprises a unitary rod having a generally rectangular configuration formed by a pair of spaced apart branches, mirror image duplicated of one another and equally spaced apart along their length.

The Steffee U.S. Pat. No. 4,611,581 entitled "Apparatus for Straightening Spinal Columns" provides an apparatus to reduce the extent of displacement between adjacent vertebra in a person's spinal column and to subsequently maintain the vertebra in a reduced displacement relationship. When the apparatus is to be installed, holes are formed in the displaced vertebra and in vertebra on opposite sides of the displaced vertebra. Force transmitting members are mounted in the holes in the vertebra. A spinal plate is then positioned on the spinal column with the force transmitting members extending outwardly through the slots in the spinal plate. Nuts are tightened on the force transmitting members connected with vertebra on opposite sides of the displaced vertebra to anchor the spinal plate in place. A nut on the force transmitting member connected with the displaced vertebra is then tightened to pull the displaced vertebra to a desired position. In one embodiment, the force transmitting member has a relatively large diameter helix which engages a side wall of the hole in the displaced vertebra. In another embodiment, an insert is positioned in a hole in the displaced vertebra and expanded by the force transmitting member to securely grip the vertebra.

A device which uses clamps as opposed to bone screws is the Asher U.S. Pat. No. 4,773,402 entitled "Dorsal Transacral Surgical Implant" wherein a pair of spine engageable rods, contoured to the desired spinal column configuration are provided with a yoke and foot element being attached to the pair of rods during use.

The Sherman U.S. Pat. No. 4,887,596 shows a pedicle screw for use in internal fixation of the spine comprising a shaft threaded at one end for insertion into a bone and at the other end having a yoke for receiving a rod, the yoke having a cusp adapted to bear against the rod and clamps for holding the rod against the cusp while permitting adjustment of the angle between the rod and the yoke.

One of the problems with the application of a spinal fixation system is the adjustability of the connective structures such as a plate with respect to a plurality of spaced apart bone screws.

SUMMARY OF THE INVENTION

It is thus an object of the present invention to provide a fixation system that offers a strong and stable construct for maximum fusion augmentation and yet is versatile enough for any patent and is easy to use.

One of the features of the present invention is a countersunk interface between the bone bolt and the plate. A countersunk interface is also located between a washer and nut. This improved construction provides some micromotion, better stress distribution, and thus enhanced fatigue life.

Another object of the present invention is to provide an improved spinal fixation apparatus having improved fit through the use of a fine adjustment between adjacent bolts/screws. This high resolution allows each screw and/or bolt to be placed anatomically with little manipulation to make the plate fit the bolts and screws of the system.

Also, the present invention provides an improved spinal fixation system that allows the surgeon to choose the amount of rigidity needed for each patient and his particular indication.

BRIEF DESCRIPTION OF THE DRAWINGS

For a further understanding of the nature and objects of the present invention, reference should be made to the following detailed description take in conjunction with the accompanying drawings, in which like parts are given like reference numerals, and wherein:

FIG. 1 is an perspective exploded view of the preferred embodiment of the apparatus of the present invention;

FIG. 1A is a fragmentary view of the preferred embodiment of the apparatus of the present invention;

FIG. 1B is a sectional, fragmentary view of the preferred embodiment of the apparatus of the present invention;

FIG. 1C is a fragmentary view of the preferred embodiment of the apparatus of the present invention;

Figure 2:
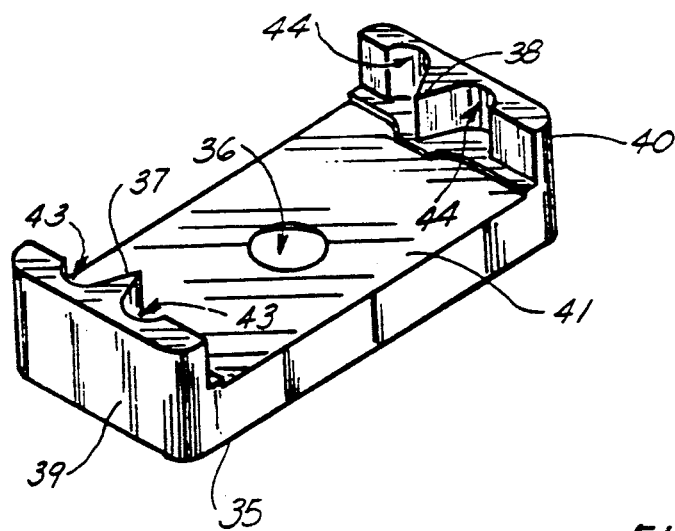
FIG. 2 is a partial perspective view of the preferred embodiment of the apparatus of the present invention.

DETAILED DESCRIPTION OF THE PREFERRED EMBODIMENT:

FIGS. 1 and 1A–1C illustrate the preferred embodiment of the apparatus of the present invention designated generally by the numeral 10. In FIG. 1 there can be seen bone bolt 11 having a shank portion 12 with a coarse thread 13 thereon. At the upper end portion of bone bolt 11, a fine thread 14 is provided. The middle portion 15 of bone bolt 11 is in the form of a hexagonal bolt which can be formed as an integral portion of the bone bolt 11. A hexagonal tool socket 16 is preferably provided at the upper end portion of bone bolt 11, for receiving an allen wrench or the like for installation of the screw into a surgical opening.

Plate 17 includes an upper surface 17A and a lower surface 17B. The plate 17 is elongated and provides curved end portions 18, 19. A longitudinally extending slot 20 includes semicircular end portions 21, 22. Slot 20 is surrounded by parallel side walls 23, 24. The slot 20 includes an upper beveled edge 25 and a lower beveled edge 26 which communicate with the slot at the top 17A and bottom 17B of plate 17. The beveled edges 25, 26 can interface with similarly shaped surfaces of the bone bolt 11 mid portion 15 (FIG. 1B).

The outer peripheral surface of plate 17 includes a plurality of spaced apart teeth 27, 28 along the sides of plate 17 (FIG. 1) which define an adjustment distance of for example just a few millimeters. Thus, spaces 29, 30 are provided between teeth 27, 28 for receiving projections 37, 38 of load washer 35. The washer 35 includes side walls 39, 40 which are spaced apart and which connect to the plate transverse flange member 41.

An opening 36 in washer 35 includes a hemispherical concave surface 42 that is similarly shaped to the hemispherical convex surface 32 of nut 31. Nut 31 includes internal threads 33 that engage the fine threads 14 of the bone bolt 11 and an upper flat surface 34.

Projections 37, 38 are correspondingly shaped to register the spaces or recesses 29, 30 between teeth 27, 28. Each projection 37, 38 has a pair of recesses 43, 44 on the sides thereof.

Figure 3:
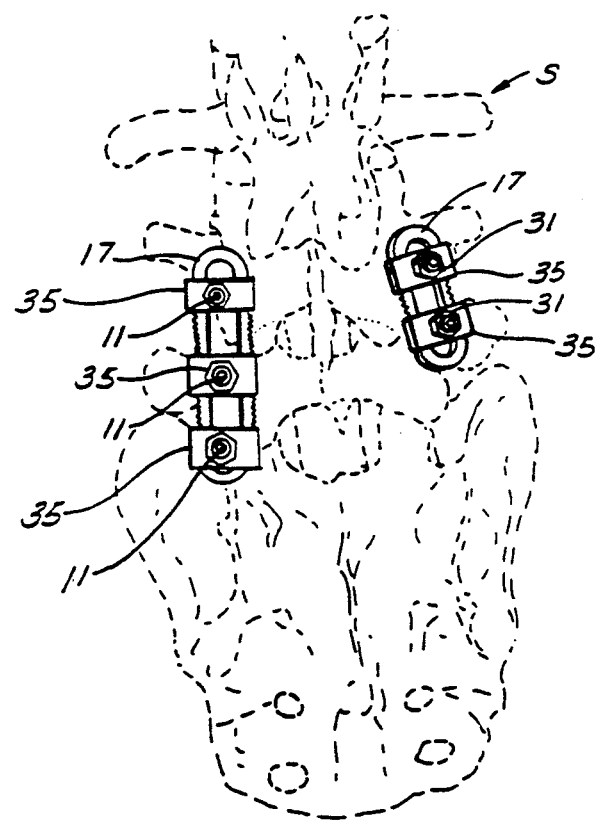
FIG. 3 is a schematic view illustrating the preferred embodiment of the apparatus of the present invention in use as part of a spinal fixation system.

FIG. 3 illustrates a pair of spaced apart plates 17 illustrating the attachment of bone bolts 11 and load transfer washers 35 as part of an overall spinal fixation system. Also illustrated is the nut 31 which threadably engages the top of the bone bolt 11. In phantom lines, the spine of the patient is illustrated generally by the letter S. It should be understood however that the surgeon can select surgical openings at particular locations to which bone bolts 11 are to be affixed and can further custom select the particular plate 17 including a particular length to accommodate one or more bone screws as part of the spinal fixation system.

Figures 4, 4A:
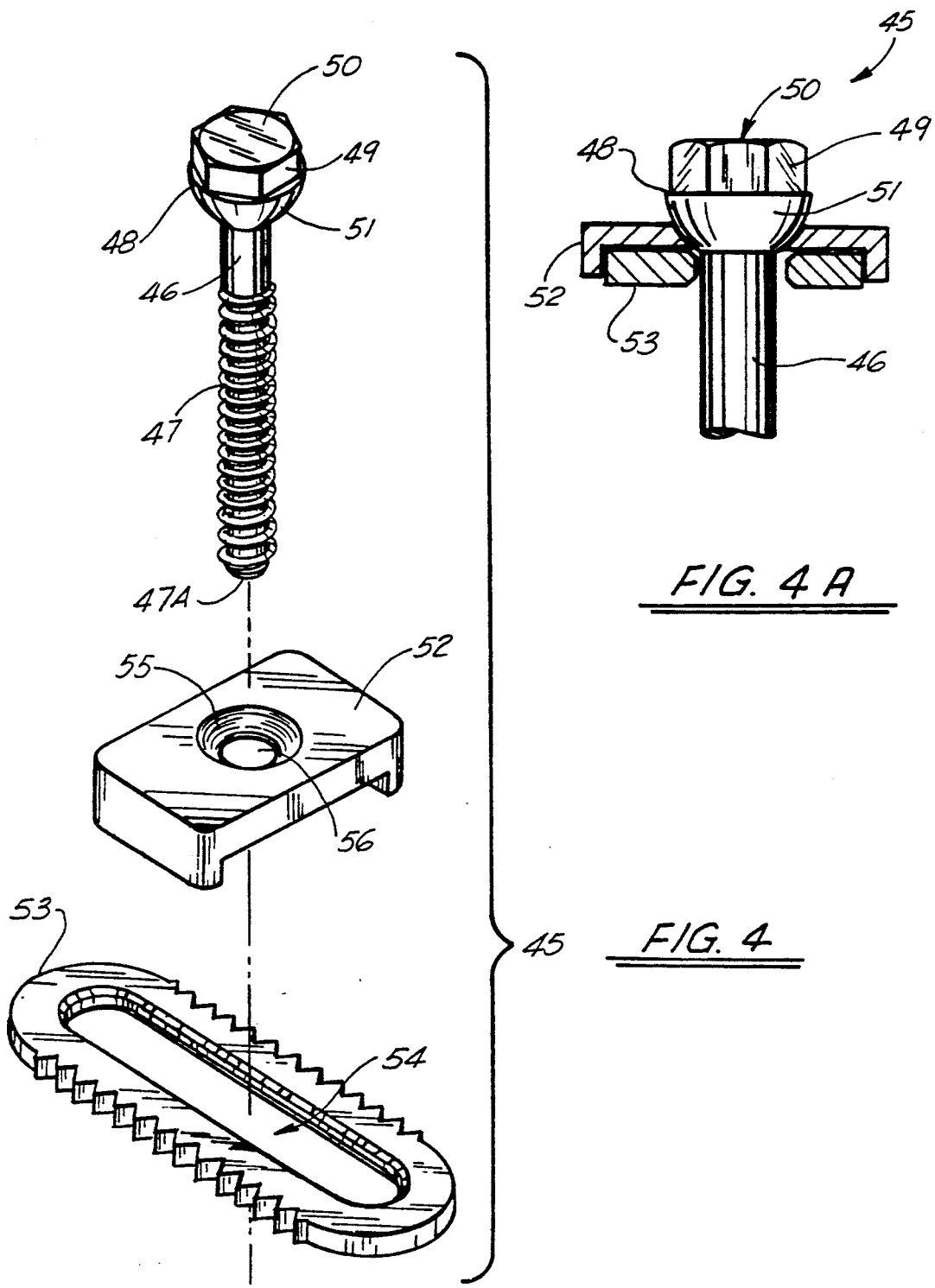
FIG. 4 is a perspective exploded view of an alternate embodiment of the apparatus of the present invention.
FIG. 4A is a sectional, fragmentary view of the alternate embodiment of the apparatus of the present invention.

In FIGS. 4 and 4B, a second alternate embodiment of the apparatus of the present invention is shown designated generally by the numeral 45. In FIG. 4, there can be seen bone screw 45 having a shank 46 portion with a coarse thread 47 thereon. At the upper end portion of bone screw 45, an enlarged head portion 48 is provided that includes a hexagonal portion 49 having a flat upper surface 50, and communicating with a hemispherically shaped lower surface 51 that can be integrally formed with hexagonal portion 49 and with shank 46 (FIG. 4A). The flat upper surface 50 could have an internally threaded portion for connecting with a stabilizing bar. Coarse threads 47 extend to the lower end portion of shank 46, terminating at 47A, as shown in FIG. 4.

Washer 52 can be of the same construction as the washer 35 described with regard to the preferred embodiment of FIGS. 1–3. Similarly, the plate 53 could be the same construction as the plate 17 described above and with regard to the preferred embodiment of FIGS. 1–3.

In FIG. 4A, a partial elevational view of bone screw 45 is shown, illustrating the upper end portion of the screw 45 including the shank 46 and head 48 portions in operating position with plate 53 and washer 52. The plate 53 provides a slot 54, and the washer 52 provides a hemispherical socket 55 communicating with and extending around opening 56. In this manner, the hemispherical surface 51 of bone screw 45 nests in and registers with the hemispherical concave surface 55 of washer 52. Bone screw 45 shank 46 passes through opening 56 and slot 54.

Table 1 below lists a summary of the parts including the part number and corresponding description as used herein and in the drawings.

TABLE 1

| Part No. | PARTS LIST Description |
|---|---|
| 10 | bone fixation apparatus |
| 11 | bone bolt |
| 12 | shank |
| 13 | coarse thread |
| 14 | fine thread |
| 15 | mid portion |
| 16 | hexagonal socket |
| 17 | plate |
| 17A | upper surface |
| 17B | lower surface |
| 18 | curved end of plate |

TABLE 1-continued

PARTS LIST

| Part No. | Description |
| --- | --- |
| 19 | curved end of plate |
| 20 | slot |
| 21 | semicircular end wall |
| 22 | semicircular end wall |
| 23 | parallel side walls |
| 24 | parallel side walls |
| 25 | bevelled edges (upper) |
| 26 | bevelled edges (lower) |
| 27 | teeth |
| 28 | teeth |
| 29 | spaces |
| 30 | spaces |
| 31 | nut |
| 32 | hemispherical convex surface |
| 33 | thread |
| 34 | lower surface |
| 35 | washer |
| 36 | opening |
| 37 | toothed projection |
| 38 | toothed projection |
| 39 | sidewall of washer 35 |
| 40 | sidewall of washer 35 |
| 41 | transverse flange |
| 42 | hemispherical concave surface |
| 43 | recess |
| 44 | recess |
| 45 | bone screw |
| 46 | shank |
| 47 | coarse threads |
| 47A | end of threads |
| 48 | enlarged head |
| 49 | hexagonal portion |
| 50 | flat upper surface |
| 51 | hemispherical convex surface |
| 52 | washer |
| 53 | plate |
| 54 | slot |
| 55 | hemispherical countersunk/concave surface |
| 56 | opening |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A bone fixation apparatus, comprising:
   a) bone bolt means having first end portions configured to be surgically implanted into a patient's bone tissue and at first and second spaced apart positions on the bone tissue;
   b) a central non-threaded section of the bone bolt means having a load transfer surface;
   c) the bone bolt means having a threaded section for threadably receiving a nut and a lower threaded section for engaging the patient's bone tissue;
   d) a plate member having upper and lower surfaces and parallel opposed outer edges with an elongated slot having a slot central longitudinal axis and surrounded by a peripheral portion having said parallel opposed outer edges;
   e) the edges carrying fine adjustment means extending between the upper and lower surfaces for defining fine adjustment positions of the bone bolt with respect to the plate; and
   f) a load transfer washer interfacing the plate member and the bone bolt means, for distributing load from the bone bolt means to the plate member, and side portions of the washer for engaging the fine adjustment means at the outer edges of said plate and affixing the position of the bone bolt with respect to the plate, and an opening in the washer for placement of a portion of the bone bolt means therethrough.

2. The apparatus of claim 1 wherein the load transfer washer includes a washer having a first flange that extends across the slot between the edges and a pair of intersecting flanges extending at angles thereto.

3. The apparatus of claim 1 wherein the slot is sized to accommodate a pair of spaced apart and surgically implanted bone bolts that comprise the bone bolt means.

4. The apparatus of claim 1 wherein the fine adjustment means includes teeth spaced along the edges.

5. The apparatus of claim 4 wherein the fine adjustment means includes regularly spaced teeth spaced along each of the edges and corresponding teeth on the washer for engaging the teeth of the edges.

6. The apparatus of claim 1 wherein the washer has an opening therein with a center that corresponds with the central longitudinal axis of the slot during use.

7. The apparatus of claim 1 wherein the washer includes a recess that corresponds with the plate so that the washer slides upon the plate at the recess.

8. The apparatus of claim 1 wherein the washer has a first center flange portion and a pair of side flanges that are spaced apart and connected to the center flange, and the side flanges are respectively positioned to bear against the edges of the plate member.

9. The apparatus of claim 1 further comprising a nut with a spherical lower surface and the load transfer washer opening is spherically shaped to receive the nut.

10. A bone fixation apparatus, comprising:
    a) bone bolt means having an integral shank portion with a first threaded end portion configured to be surgically implanted into a patient's bone tissue and at first and second spaced apart positions on the bone tissue;
    b) a central integral, non-threaded section of the bone bolt means defining a bone bolt means thickness and having a longitudinally extending, shaped load transfer surface;
    c) the bone bolt means having a second threaded end portion for threadably receiving a nut; and
    d) a bone plate member having upper and lower surfaces and parallel opposed outer edges with an elongated slot with a central longitudinal axis surrounded by a peripheral portion having said parallel outer opposed edges, the plate lower surface being countersunk at the slot to fit the bone bolt load transfer surface, and the slot being sized to receive the second threaded section of the bone bolt.

11. The apparatus of claim 10 wherein the edges carry closely spaced fine adjustment means extending between the upper and lower surfaces for affixing the bone bolt with respect to the plate in a selected position and including several adjustment positions per the thickness of the bone bolt means.

12. The apparatus of claim 11 further comprising a load transfer washer interfacing the plate member and the bone bolt means, for distributing load from the bone bolt means to the plate member and including sidewall portions of the washer for engaging the fine adjustment means at the edges, and an opening in the washer for placement of a portion of the bone bolt means therethrough.

13. The apparatus of claim 10 wherein the load transfer washer includes a washer having a first flange that extends across the slot between the edges and a pair of intersecting flanges extending at angles thereto.

14. The apparatus of claim 13 wherein the fine adjustment means includes regularly spaced teeth spaced along each of the edges and corresponding teeth on the washer for engaging the teeth of the edges.

15. The apparatus of claim 10 wherein the slot is sized to accommodate a pair of spaced apart and surgically implanted bone bolts that comprise the bone bolt means.

16. The apparatus of claim 10 wherein the fine adjustment means includes a plurality of teeth spaced along the edges.

17. The apparatus of claim 16 wherein the opening has a surrounding hemispherical portion that receives a corresponding hemispherical portion of the nut.

18. The apparatus of claim 10 further comprising a nut with a curved angular lower surface and wherein the washer has an opening therein with a center that corresponds with the central longitudinal axis of the slot during use, and the opening is shaped corresponding to the nut for receiving the nut.

19. The apparatus of claim 10 wherein the washer includes a recess that corresponds with the plate so that the washer slides upon the plate at the recess.

20. The apparatus of claim 10 wherein the washer has a center flange and a pair of spaced apart side flanges that are positioned to engage the edges of the plate member during use.

21. The apparatus of claim 10 further comprising a nut with a spherical lower surface and the load transfer washer opening is spherically shaped to receive the nut.

22. The apparatus of claim 10 wherein the slot has a lower beveled surface and the bone bolt has a corresponding surface that abuts the beveled surface for load transfer.

23. A bone fixation system, comprising:
a) bone bolt means having first end portions configured to be surgically implanted into a patient's bone tissue at a first and second spaced apart positions on the bone tissue;
b) a central non-threaded section of the bone bolt means having a load transfer surface;
c) the bone bolt means having a second section with threads thereon for threadably receiving a nut;
d) a plate member having upper and lower surfaces and parallel opposed outer edges with an elongated slot surrounded by a peripheral portion having said parallel opposed outer edges;
e) load transfer washer means interfacing the plate member and the bone bolt means for distributing load from the bone bolt means to the plate member;
f) a countersunk opening for receiving a nut in the washer means for placement of a portion of the bone bolt means therethrough; and
g) a nut having a longitudinally extending shaped portion that fits the washer at the countersunk opening.

24. A bone fixation apparatus, comprising:
a) bone screw means having first end portions configured to be surgically implanted into a patient's bone tissue at a first and second spaced apart positions on the bone tissue;
b) a bone plate member having upper and lower surfaces and parallel opposed outer edges with an elongated slot with a central longitudinal axis and surrounded by a peripheral portion having said parallel opposed outer edges;
c) the edges carrying fine adjustment means extending between the upper and lower surfaces for defining adjustment positions of the bone screw with respect to the plate; and
f) a load transfer washer interfacing the plate member and the bone screw means for distributing load from the bone screw means to the plate member, and having a main body including side portions of the washer for engaging the fine adjustment means at the outer edges of said plate and affixing the position of the bone screw with respect to the plate, and an opening in the washer for placement of a portion of the bone screw means therethrough.

25. The apparatus of claim 24 wherein the load transfer washer includes a washer having a first flange that extends across the slot between the edges and a pair of intersecting flanges extending at angles thereto.

26. The apparatus of claim 24 wherein the slot is sized to accommodate a pair of spaced apart and surgically implanted bone screws that comprise the bone screw means.

27. The apparatus of claim 24 wherein the fine adjustment means includes teeth spaced along the edges.

28. The apparatus of claim 27 wherein the fine adjustment means includes regularly spaced teeth spaced along each of the edges and corresponding teeth on the washer for engaging the teeth of the edges.

29. The apparatus of claim 24 wherein the washer has an opening therein with a center that corresponds with the central longitudinal axis of the slot during use.

30. The apparatus of claim 24 wherein the washer includes a recess that corresponds with the plate so that the washer slides upon the plate at the recess.

31. The apparatus of claim 24 wherein the washer has a center flange and two side flanges that are spaced apart, connected to the center flange, and positioned respectively to bear against the edges of the plate member.

* * * * *